(12) United States Patent
Seidenfeld et al.

(10) Patent No.: US 11,596,551 B2
(45) Date of Patent: Mar. 7, 2023

(54) WEIGHTED SLEEP MASK

(71) Applicant: Gravity Products LLC, Brooklyn, NY (US)

(72) Inventors: Justin Seidenfeld, Brooklyn, NY (US); Yuk Cheung Wong, Brooklyn, NY (US); Wing Hin Ng, Brooklyn, NY (US); Michael James Grillo, Brooklyn, NY (US)

(73) Assignee: Gravity Products, LLC, Brooklyn, NY (US)

( * ) Notice: Subject to any disclaimer, the term of this patent is extended or adjusted under 35 U.S.C. 154(b) by 0 days.

(21) Appl. No.: 17/062,244

(22) Filed: Oct. 2, 2020

(65) Prior Publication Data

US 2021/0015671 A1 Jan. 21, 2021

Related U.S. Application Data

(63) Continuation of application No. 17/006,141, filed on Aug. 28, 2020, now abandoned, and a continuation of application No. 16/290,781, filed on Mar. 1, 2019, now abandoned, and a continuation of application No. 29/682,171, filed on Mar. 1, 2019, now Pat. No. Des. 906,405.

(51) Int. Cl.
| | |
|---|---|
| *A61F 9/04* | (2006.01) |
| *A61F 7/02* | (2006.01) |
| *A61M 21/00* | (2006.01) |
| *A61F 7/00* | (2006.01) |

(52) U.S. Cl.
CPC ............ *A61F 9/04* (2013.01); *A61F 7/02* (2013.01); *A61M 21/00* (2013.01); *A61F 2007/0004* (2013.01); *A61F 2007/023* (2013.01); *A61M 2021/0022* (2013.01); *A61M 2021/0066* (2013.01)

(58) Field of Classification Search
CPC ........ A61F 9/04; A61F 7/02; A61F 2007/023; A61F 2007/0004; A61M 21/00; A61M 2021/0066; A61M 2021/0022
USPC ........................................................ 2/215
See application file for complete search history.

(56) References Cited

U.S. PATENT DOCUMENTS

| | | | | |
|---|---|---|---|---|
| 3,173,419 | A * | 3/1965 | Dubilier | A61M 21/00 607/109 |
| 4,243,041 | A * | 1/1981 | Paul | A61F 7/10 351/124 |
| 4,460,645 | A * | 7/1984 | Jones | A41D 31/04 428/323 |
| 4,520,510 | A * | 6/1985 | Daigle | A61F 9/029 2/12 |

(Continued)

*Primary Examiner* — Katharine G Kane
(74) *Attorney, Agent, or Firm* — Bochner IP, PLLC; Andrew D. Bochner

(57) ABSTRACT

A sleep mask is created comprising a sleep mask cover that can accommodate a weighted mask component and a thermal mask component. The sleep mask cover may include a fastening mechanism at the opening which may be removably engaged or disengaged to disable or enable, respectively, access to the opening for insertion of the weighted mask component and the thermal mask component. The weighted mask component may include a set of eye panels that are devoid of weight material to prevent unwanted pressure on a human user's eyes when the sleep mask is worn around the head of a human user. Further, the weighted mask component may include a pocket for insertion of the thermal mask component.

20 Claims, 9 Drawing Sheets

(56) References Cited

U.S. PATENT DOCUMENTS

| | | | | |
|---|---|---|---|---|
| 4,790,031 | A * | 12/1988 | Duerer | A61F 9/02 128/858 |
| 4,872,217 | A * | 10/1989 | Kitayama | A61F 9/04 2/15 |
| 5,046,604 | A * | 9/1991 | Forhetz | A61L 9/01 206/524.5 |
| 5,575,009 | A * | 11/1996 | Ryvin | A41D 13/1153 2/173 |
| 5,628,772 | A * | 5/1997 | Russell | A61F 7/10 601/112 |
| 6,223,748 | B1 * | 5/2001 | Chaves | A61F 9/04 128/857 |
| 9,795,502 | B1 * | 10/2017 | Kopes | A61F 7/007 |
| 2003/0014096 | A1 * | 1/2003 | Burkhart | A61F 7/02 607/109 |
| 2005/0229281 | A1 * | 10/2005 | Glasser | A61F 9/04 2/15 |
| 2008/0009926 | A1 * | 1/2008 | Russak | A61F 7/02 607/109 |
| 2010/0312317 | A1 * | 12/2010 | Baltazar | A61F 7/02 607/109 |
| 2011/0178585 | A1 * | 7/2011 | Biser | A61F 7/02 607/109 |
| 2011/0208279 | A1 * | 8/2011 | Sanker | A61F 7/02 607/109 |
| 2014/0288624 | A1 * | 9/2014 | Wasko | A61F 7/02 607/109 |
| 2014/0331383 | A1 * | 11/2014 | Bially | A61F 9/04 2/173 |
| 2015/0173487 | A1 * | 6/2015 | Wardaszka | A45D 44/002 604/303 |
| 2016/0008175 | A1 * | 1/2016 | Bergman | A61F 9/04 2/171.2 |
| 2016/0051402 | A1 * | 2/2016 | Laghi | A61F 7/02 607/109 |
| 2016/0120692 | A1 * | 5/2016 | Chen | A61F 7/03 607/109 |
| 2017/0020767 | A1 * | 1/2017 | DeMarie | A61H 23/02 |
| 2017/0209309 | A1 * | 7/2017 | Lazor | A61F 9/04 |
| 2017/0231813 | A1 * | 8/2017 | Huang | A61F 7/034 607/109 |
| 2017/0296380 | A1 * | 10/2017 | Barger | A61F 7/02 |
| 2019/0015296 | A1 * | 1/2019 | Takehara | C01B 3/065 |
| 2019/0274454 | A1 * | 9/2019 | Bidhendi | A45C 13/10 |

* cited by examiner

WEIGHTED SLEEP MASK

CROSS-REFERENCE TO RELATED APPLICATIONS

This application is a continuation of U.S. application Ser. No. 17/006,141 filed on Aug. 28, 2020, entitled "WEIGHTED SLEEP MASK", and is a continuation application of U.S. application Ser. No. 16/290,781 filed on Mar. 1, 2019, entitled "WEIGHTED SLEEP MASK", and further claims priority to U.S. Design application No. 29/682,171, filed on Mar. 1, 2019, entitled "WEIGHTED SLEEP MASK." the entire disclosures of which are hereby incorporated herein by reference.

FIELD OF THE DISCLOSURE

The present disclosure relates to exemplary embodiments of a sleep mask, and more particularly, to exemplary embodiments of a sleep mask having a weighted component within the sleep mask.

BACKGROUND INFORMATION

In many environments, various people can encounter difficulty in achieving restful sleep due to unwanted light levels within these environments. For example, in an aircraft, cabin lights may make it difficult for a person to achieve restful sleep. As a result, people that encounter such difficulty in achieving restful sleep due to these unwanted light levels may resort to using various devices, including sleep masks, to block out these unwanted light levels and make it easier to achieve restful sleep. However, these devices may be cumbersome and become undone as a result of movement during sleep. This may interrupt a person's ability to achieve restful sleep over a significant period, leaving the person tired and with less energy.

SUMMARY OF EXEMPLARY EMBODIMENTS OF THE DISCLOSURE

Exemplary embodiments of the present disclosure can provide for a sleep mask comprising a sleep mask cover comprising a front cover component, a rear cover component, and an opening, and a weighted component that is removably inserted into the opening of the sleep mask cover and configured to be placed between the front cover component and the rear cover component, the weighted component comprising a plurality of separate compartments each having weighted material placed within the compartments.

In some exemplary embodiments, the sleep mask can further comprise a plurality of dividers to separate each of the plurality of separate compartments so that the weighted materials is distributed within each of the compartments. The weighted component can further comprise a forward panel and a rear panel, wherein the plurality of separate components are provided between the forward panel and rear panel. The plurality of dividers can comprise stitches provided between the forward panel and rear panel of the weighted component.

In some exemplary embodiments, the sleep mask can further comprise a panel provided at an eye portion of the weighted component distinct from the plurality of separate compartments, wherein the panel contains no weighted material provided within the panel. The panel can comprise two panels and the plurality of separate compartments containing weighted material surround the two panels.

In some exemplary embodiments, the sleep mask can further comprise a first strap component attached to the sleep mask cover at a first side of the sleep mask cover, and a second strap component attached to the sleep mask cover at a second side of the sleep mask cover opposite the first side. In some exemplary embodiments, the sleep mask can further comprise a closing mechanism configured to open and close the opening, wherein the opening is provided at a top portion of the sleep mask cover between the front cover component and the rear cover component. In some exemplary embodiments, the weighted component can have a similar size and shape as the sleep mask cover. The weighted material can comprise beads made of glass.

In some exemplary embodiments, a sleep mask is provided comprising a sleep mask cover comprising a front cover component and a rear cover component, and a weighted component provided between the front cover component and the rear cover component, the weighted component comprising a top portion having weighted material configured to be placed above a user's eyes, a bottom portion having weighted material configured to be placed below a user's eyes, and a middle portion between the top portion and bottom portion, the middle portion configured to be placed on a user's eyes, wherein the middle portion does not contain any weighted material.

In some exemplary embodiments, the sleep mask can further comprise two panel areas in the middle portion configured to be placed on a user's eyes, wherein the two panel areas do not contain weighted material and a remaining portion of the middle portion comprises weighted material. In some exemplary embodiments, the sleep mask can further comprise a plurality of dividers that separate the top portion, middle portion and bottom portion such that the weighted material is distributed within each portion. In some exemplary embodiments, the sleep mask can further comprise an opening provided between the front cover component and the rear cover component, wherein the weighted component is configured to be removably inserted within the opening. In some exemplary embodiments, the sleep mask can further comprise a closing mechanism configured to open and close the opening, wherein the opening is provided at a top portion of the sleep mask cover between the front cover component and the rear cover component. The weighted material can comprise beads made of glass.

In some exemplary embodiments, a sleep mask is provided comprising a sleep mask cover comprising a front cover component and a rear cover component, and a weighted component provided between the front cover component and the rear cover component, the weighted component comprising a first portion having weighted material and a second portion configured to be placed on a user's eyes, the second portion not containing any weighted material. In some exemplary embodiments, the second portion comprises at least two panel areas not containing any weighted material.

In some exemplary embodiments, the sleep mask can further comprise a plurality of dividers comprising stitching that separate the first portion and the second portion. In some exemplary embodiments, the weighted component further comprises a forward panel and a rear panel, wherein the plurality of dividers are provided between the forward panel and the rear panel.

BRIEF DESCRIPTION OF THE DRAWINGS

The foregoing and other objects of the present disclosure will be apparent upon consideration of the following detailed description, taken in conjunction with the accompanying drawings, and claims, in which like reference characters refer to like parts throughout, and in which:

Figure 1:
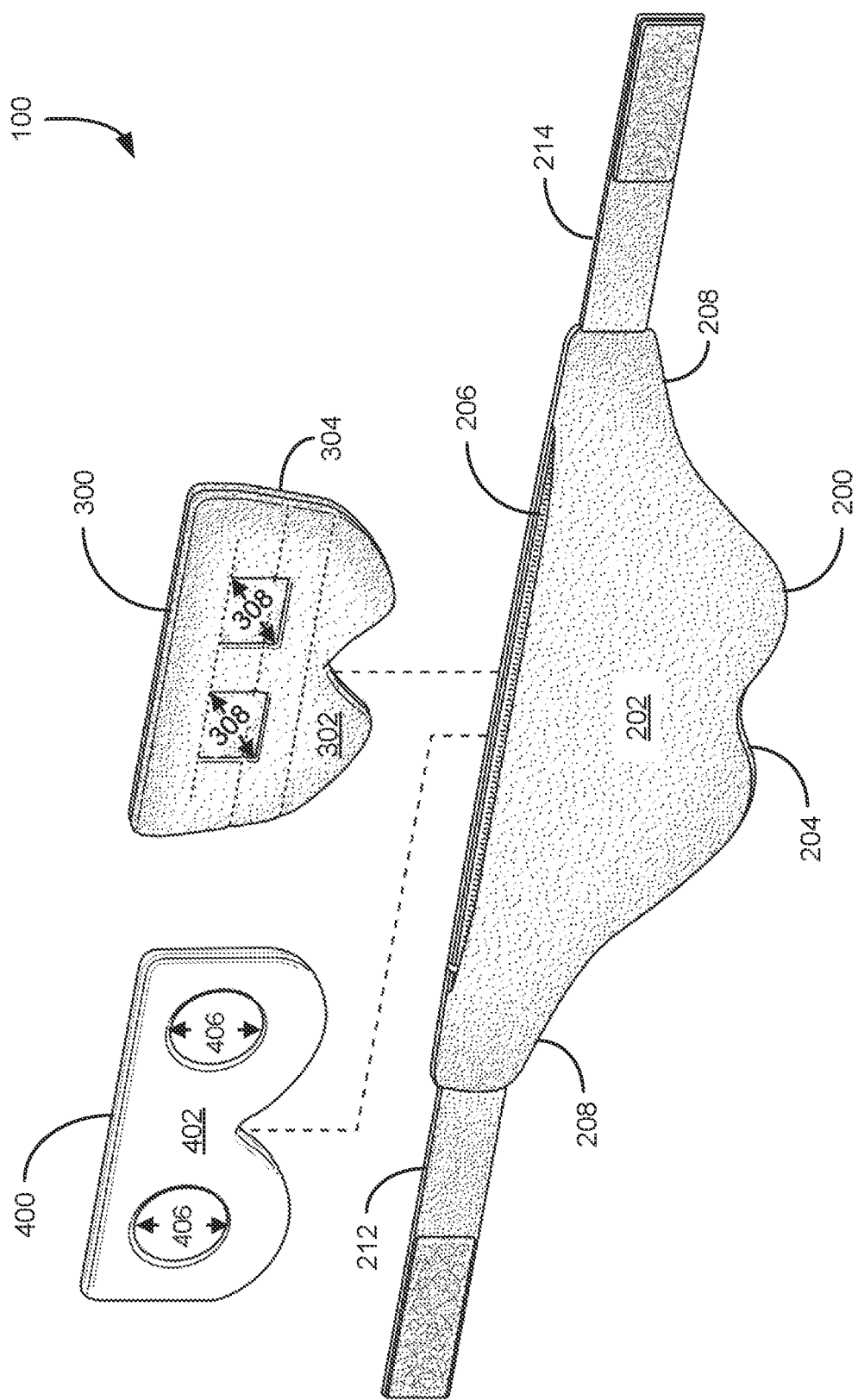
FIG. 1 is a partially exploded view of a sleep mask comprising a sleep mask cover for insertion of a weighted mask component and of a thermal mask component into an internal chamber of the sleep mask cover.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described embodiments without departing from the true scope and spirit of the subject disclosure.

DETAILED DESCRIPTION OF EXEMPLARY EMBODIMENTS OF DISCLOSURE

Techniques and systems described below relate to a sleep mask that comprises a sleep mask cover that accommodates a weighted mask component and a thermal mask component within an internal compartment of the sleep mask cover. In one example, the sleep mask cover for a sleep mask is created utilizing a front cover component and a rear cover component that may be sewn together along a peripheral edge of each cover component to attach the front cover component to the rear cover component. The front cover component and the rear cover component may have similar or identical dimensions and shape, whereby attachment of the front cover component to the rear cover component is performed such that the sleep mask cover maintains the shape of each of the individual cover components. In an example, the sleep mask cover further comprises an opening along an upper edge of the sleep mask cover (e.g., location where the front cover component and rear cover component is not sewn together) that may be used to access an internal chamber of the sleep mask cover. The periphery of the opening may include a fastening mechanism (e.g., zipper, snaps, hook and loop fasteners, etc.) that may be used to close the opening of the sleep mask cover. The sleep mask cover may further comprise a strap usable to affix the sleep mask to a human individual's head and over the individual's eyes. The strap may be affixed to the sleep mask cover on a left attachment seam and a right attachment seam of the sleep mask cover.

In an example, the sleep mask includes a weighted mask component that can be inserted into the sleep mask cover through the opening along the upper edge of the sleep mask cover. The weighted mask component may have a shape similar to the sleep mask cover to enable the weighted mask component to completely fill the internal chamber of the sleep mask cover. The weight mask component may comprise a forward panel and a rear panel that have similar dimensions and shape. In an example, the inward surface of the forward panel and the inward surface of the rear panel are sewn together along a peripheral edge of both panels, with the exception of a gap in the seam, resulting in an inside-out weighted mask component with an opening usable to introduce the weight material to the weighted mask component. Once the forward and rear panels are sewn together while leaving an opening, the weight mask component is turned rightside-out through the opening, resulting in a chamber usable to maintain the weight material within the weight mask component. In an example, the forward and rear panels are further sewn together along the outer surface of either the forward or rear panel to generate eye panels for the weighted mask component. This may prevent weight material from being distributed within the eye panels and creating pressure points over the eyes of a human individual when the sleep mask is work over the face. Additionally, the forward and rear panels may be sewn together across the length of the weighted mask component to define pockets within the chamber for distribution of the weight material. The weight material may be introduced through the gap in the seam between the forward and rear panels to achieve a desired weight for the weighted mask component. The gap is then closed by sewing the forward and rear panels together at this location.

In an example, the weighted mask component includes a thermal mask component pocket panel that may be affixed to the rear panel of the weighted mask component using elastic tape sewn to the sides of the weighted mask component and the bottom seam of the weighted mask component. This thermal mask component pocket panel may have a similar shape or profile to that of the weighted mask component. Further, the attachment of the thermal mask component pocket panel to the weighted mask component may result in the creation of a pocket usable to accommodate the thermal component of the sleep mask. In an example, the thermal mask component is created using a plastic material (e.g., polyvinyl chloride (PVC), etc.) that is filled with a thermal gel or other material that may retain heat or provide cooling for an extended period of time when the thermal mask component is introduced to a heating source or cooling source, respectively. The thermal mask component may include eye cutouts to prevent heating or cooling of a human individual's eyes when the sleep mask is affixed to the human individual's head. The thermal mask component may be created to match the contours of the weighted mask component when inserted into the thermal mask component pocket panel. For instance, the thermal mask component may be designed such that the eye cutouts align with the eye panels of the weighted mask component when inserted into the thermal mask component pocket.

In an example, the weighted mask component and the thermal mask component can be introduced into the internal chamber of the sleep mask cover through the opening along the upper edge of the sleep mask cover. To secure the weighted mask component and the thermal mask component within the internal chamber of the sleep mask cover, a user of the sleep mask may utilize the fastening mechanism installed along the opening of the sleep mask cover to close the opening and, thus, the internal chamber of the sleep mask cover. A user of the sleep mask may place the sleep mask within a heating or cooling source to heat or cool the thermal mask component within the internal chamber of the sleep mask cover, respectively. This may provide a heating or cooling effect to the user of the sleep mask when worn by the user for a period of time.

In the preceding and following description, various techniques are described. For purposes of explanation, specific configurations and details are set forth in order to provide a thorough understanding of possible ways of implementing the techniques. However, it will also be apparent that the techniques described below may be practiced in different configurations without the specific details. Furthermore, well-known features may be omitted or simplified to avoid obscuring the techniques being described.

Techniques described and suggested in the present disclosure improve the field of sleep aid devices, especially the field of manufacturing and design of sleep masks. Additionally, techniques described and suggested in the present disclosure enable selective introduction of weighted and thermal components to a sleep mask to provide customized comfort and support for users attempting to eliminate ambient light and to achieve restful sleep. Moreover, the removal of weighted and thermal components from sensitive facial areas, such as the eyes, reduces user discomfort and decreases the risk of injury to these sensitive facial areas. The strap attached to the sleep mask cover also allows for a customized and secure fit of the sleep mask around a user's face, which can reduce movement of the sleep mask during normal sleep patterns and body movements.

Figure 4:
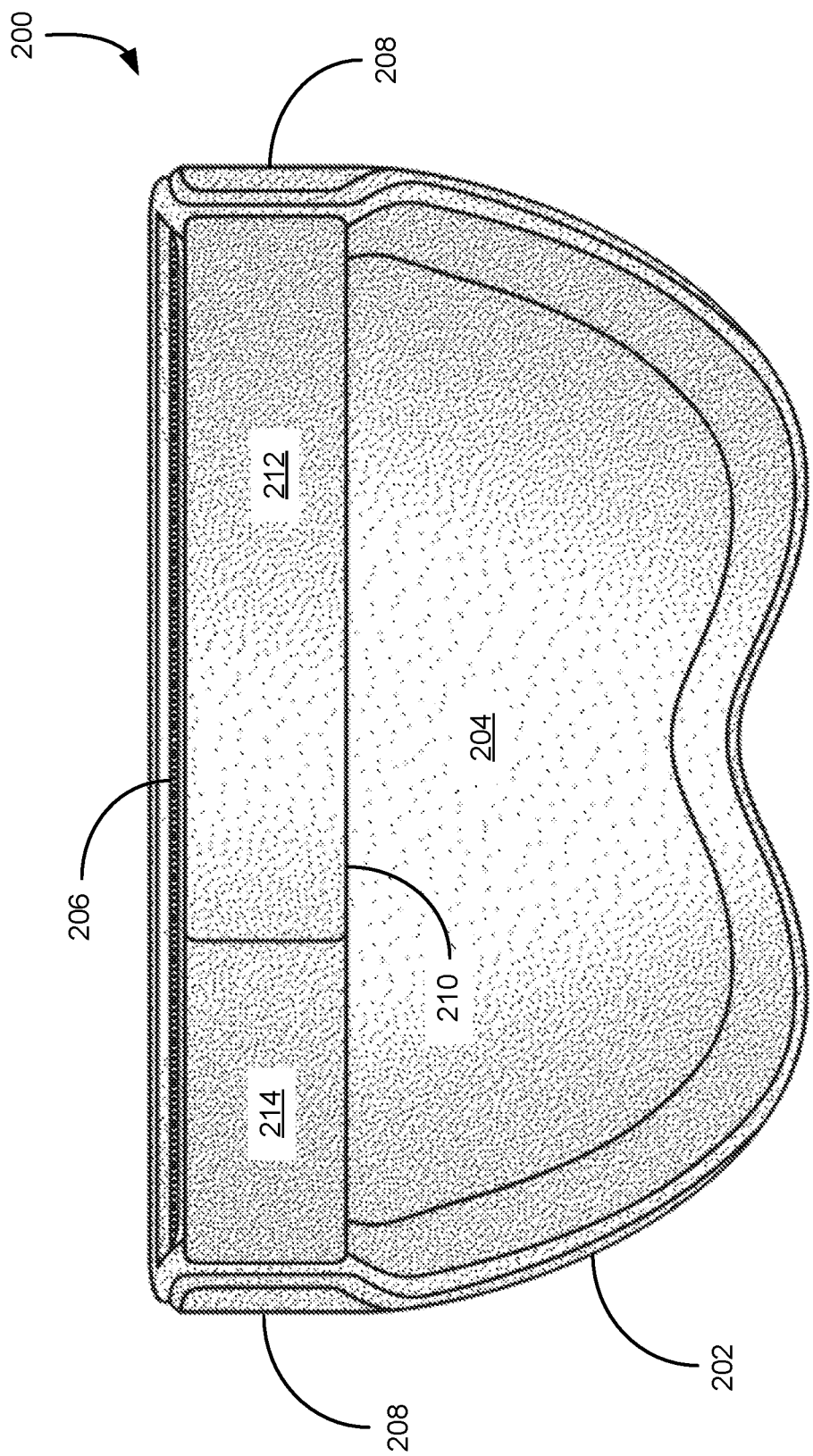
FIG. 4 is a rear view of the sleep mask cover of the sleep mask with the strap of the sleep mask cover engaged.

FIG. 1 is a partially exploded view of a sleep mask 100 comprising a sleep mask cover 200 for insertion of a weighted mask component 300 and of a thermal mask component 400 into an internal chamber of the sleep mask cover 200. The sleep mask cover 200 may be manufactured using materials that are non-toxic and comfortable when worn on a human user's face. In an embodiment, the sleep mask cover 200 comprises a front cover component 202 and, as illustrated in FIG. 4, a rear cover component 204 that are sewn together along the side and bottom peripheral edges of each of the front cover component 202 and the rear cover component 204. The upper peripheral edge of each of the front cover component 202 and the rear cover component 204 may remain unattached to create an opening to the internal chamber of the sleep mask cover 200. In an embodiment, a fastening mechanism 206 is sewn into the upper peripheral edge of the front cover component 202 and the rear cover component 204 along the opening.

This fastening mechanism 206 may be used to close the opening, preventing access to the internal chamber of the sleep mask cover 200. Further, if the opening is closed, the fastening mechanism 206 may be released to enable use of the opening to access the internal chamber of the sleep mask cover 200. In an embodiment, the fastening mechanism 206 is a zipper, which can be used to removably attach the upper peripheral edges of the front cover component 202 and the rear cover component 204 to terminate or re-introduce the opening to the internal chamber of the sleep mask cover 200. Other alternatives for the fastening mechanism 206 may be used, such as hook and loop fasteners (e.g., Velcro®, etc.), snap fasteners, buttons, clamps, and the like.

As noted above, the sleep mask cover 200 may be manufactured using materials that are non-toxic and comfortable when worn on a human user's face. In an embodiment, the front cover component 202 and the rear cover component 204 are manufactured using pleuche or any other textile having a cut nap or pile. The front cover component 202 and the rear cover component 204 may also be manufactured using other textile materials, such as: cashmere, imitation cashmere, fleece, leather, satin, suede, velvet, fustian, corduroy, flannel, tweed, polyester, micro-fiber, and the like. In an embodiment, the front cover component 202 and the rear cover component 204 can be manufactured using different materials. For example, the front cover component 202 may be manufactured using pleuche while the rear cover component 204 may be manufactured using satin. Thus, a user of the sleep mask 100 may feel the satin material when applying the sleep mask 100 while the pleuche material is exposed away from the user's face.

Figure 2:
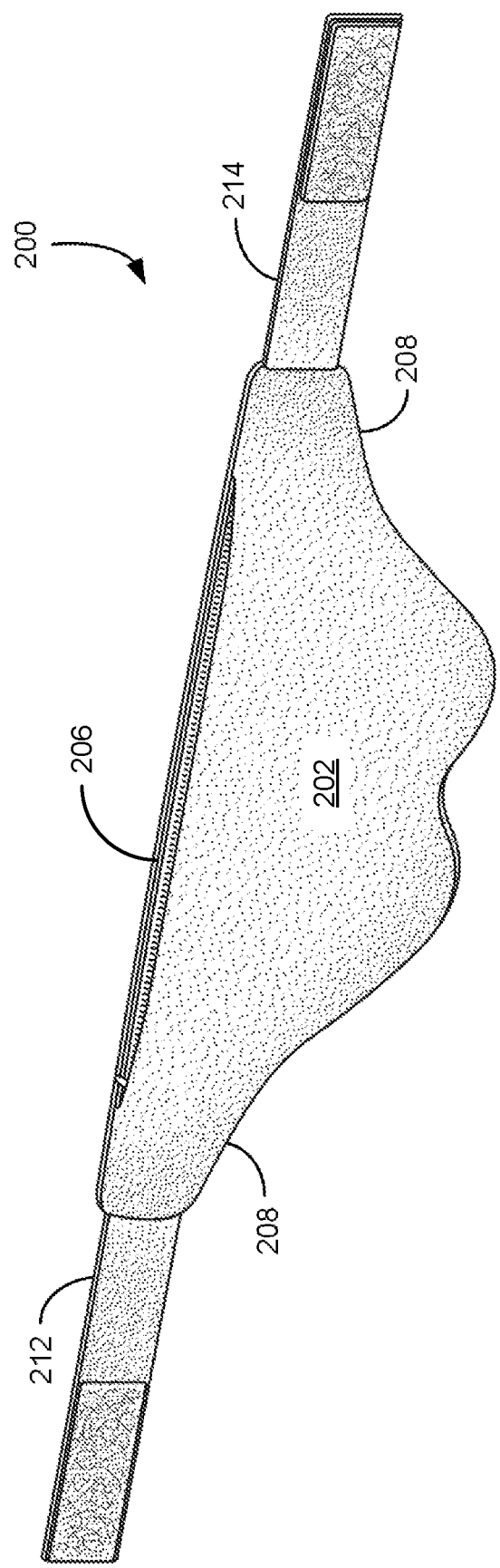
FIG. 2 is a perspective view of the sleep mask cover of the sleep mask with the strap of the sleep mask cover disengaged.
Figure 9:
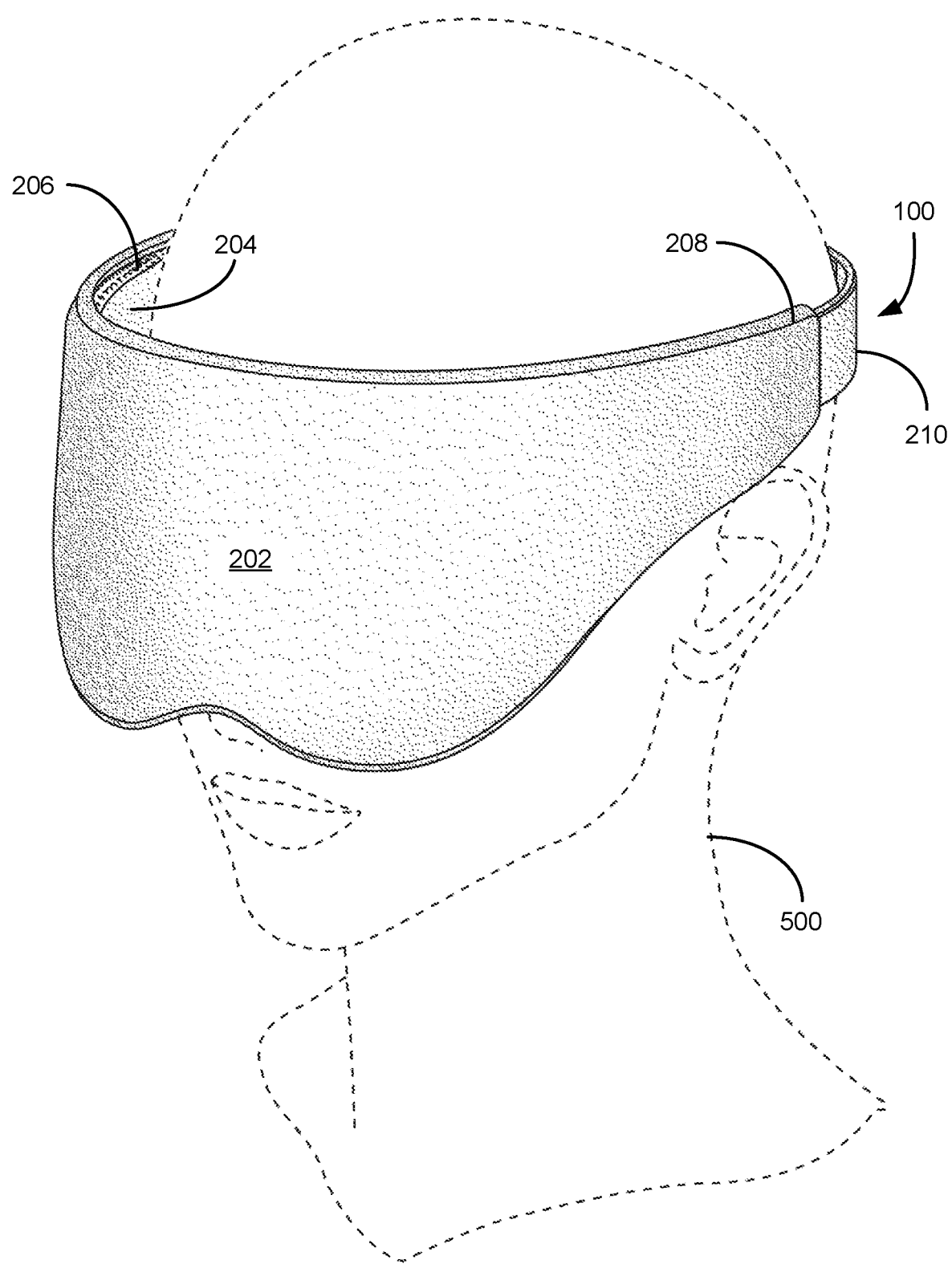
FIG. 9 is a perspective of the sleep mask as worn on the head of a human individual.

In an embodiment, as illustrated in FIG. 2, the sleep mask cover 200 includes a pair of side tabs 208 usable to attach components of a strap 210 that may be used to removably position the sleep mask 100 onto a user's head and face. For instance, a first strap component may be sewn into a first side tab of the sleep mask cover 200. This first strap component may include a fastening component that may be removably attached to a second fastening component of the second strap component to unite these strap components of the strap 210. The second strap component may be sewn into a second side tab of the sleep mask cover 200. This second strap component may include the other fastening component usable to unite the strap components of the strap 210. Thus, as illustrated in FIG. 9, a user of the sleep mask 100 may wrap the strap components of the strap 210 around its head and removably attach the fastening components together to secure the sleep mask 100 to its head. In an embodiment, the fastening components of the strap 210 are hook and loop fasteners. In an alternative embodiment, the fastening components include a clip attached to a first strap component and a clip receiver attached to a second strap component. The clip may be introduced into the clip receiver to removably attach the strap components of the strap 210. Further, the clip may include a looping mechanism that may be used to adjust the length of the first strap component. This allows the user of the sleep mask 100 to secure the sleep mask 100 around its head and face.

In an embodiment, the sleep mask cover 200 is contoured at the lower peripheral edge of the sleep mask cover 200 to accommodate the nose bridge of a human user, as illustrated in FIG. 9. For example, the distance between the upper peripheral edge and the lower peripheral edge of the sleep mask cover 200 may be five inches. Towards the center of the sleep mask cover 200, this distance may decrease at a gradual rate to four inches, creating an indentation at the bottom of the sleep mask cover 200 at the center that may be used to accommodate the nose bridge of the human user. The upper peripheral edge of the sleep mask cover, from a first end of a first side tab to a second end of the second side tab, may be fifteen inches in length. Each side tab 208 may measure up to three inches in length in order to accommodate the different strap components usable to securely place the sleep mask 100 over a human user's head and face. Thus, the opening to the internal chamber and the fastening mechanism 206 usable to engage the front cover component 202 and the rear cover component 204 at the opening may be up to nine inches in length. Each strap component of the strap 210 may be at least 5.5 inches in length to enable wrapping of these strap components around a human user's head and face and to allow adjustment of the strap 210 for a secure fit of the sleep mask 100. It should be noted that the dimensions described above are utilized to provide an illustrative example of the possible shape of the sleep mask 100 and the sleep mask cover 200 and may be adjusted or tailored to accommodate the contours of a human head and face.

In an embodiment, the sleep mask 100 also includes a weighted mask component 300 that can be inserted into the internal chamber of the sleep mask cover 200 through the opening when the fastening mechanism 206 is not engaged, exposing the internal chamber of the sleep mask cover 200. The weighted mask component 300 may be manufactured using non-toxic materials that may be resistant to thermal changes caused by the heating or cooling of the thermal mask component 400. In an embodiment, the weighted mask component 300 is manufactured using an elastic polyurethane fabric, such as elastane or spandex. Other elastic materials that may withstand repeated heating and cooling cycles may also be used in manufacturing the weighted mask component 300.

Figure 7:
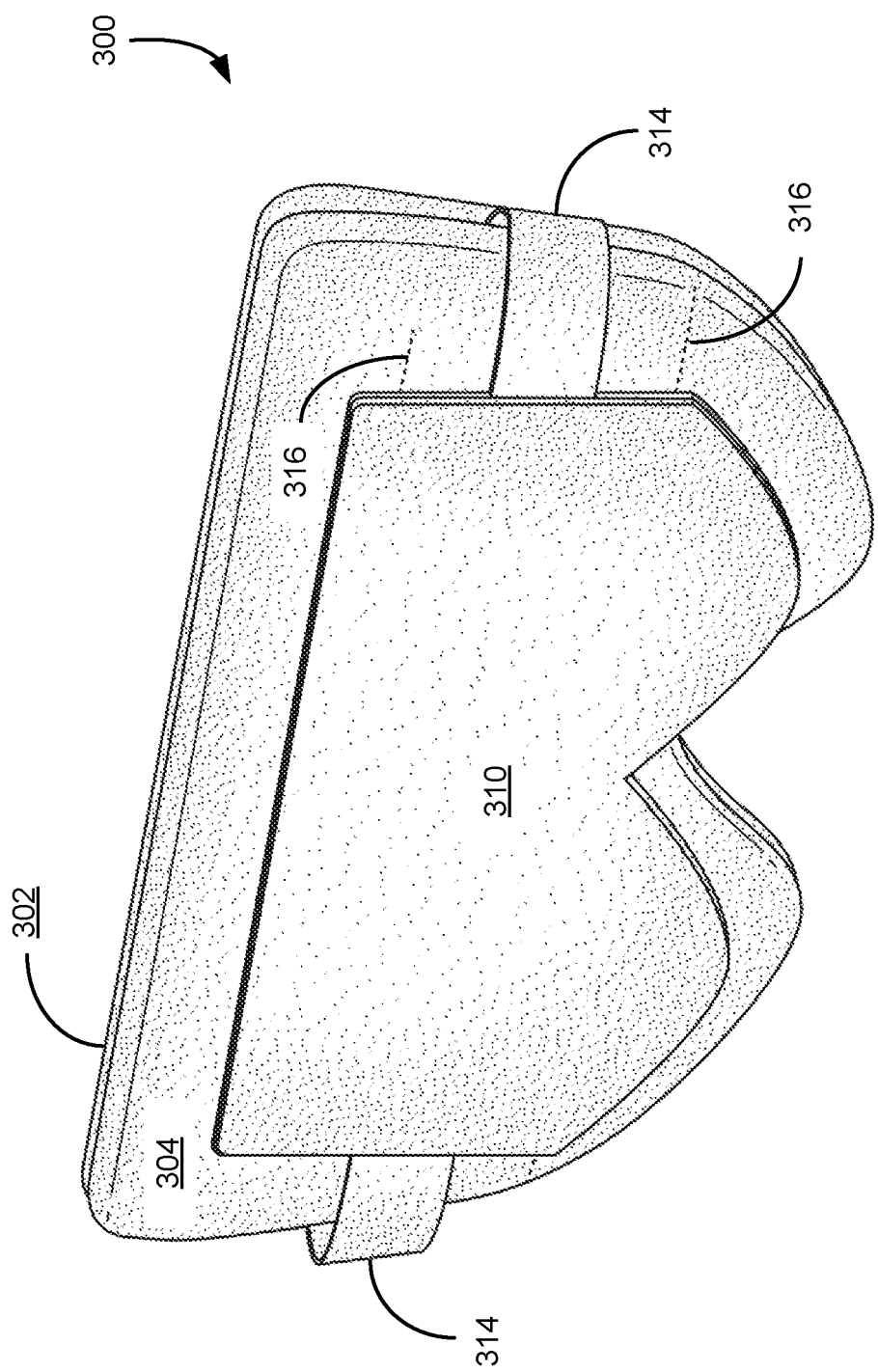
FIG. 7 is a perspective rear view of the weighted mask component of the sleep mask.

The weighted mask component 300 may include a forward panel 302 and, as illustrated in FIG. 7, a rear panel 304 that may be sewn together to create a weight chamber usable to introduce weight material into the weighted mask component 300. To manufacture the weighted mask component 300, the outward facing surfaces of the forward panel 302 and the rear panel 304 may be sewn together along the peripheral edge of each panel 302, 304 while leaving a gap on a side segment of the peripheral edge. This may result in the creation of the weighted mask component 300 in an inside-out state with an opening that may be used to invert the weighted mask component 300 into its proper configuration and to enable access to the weight chamber. This process may preserve the stitching of the panels 302, 304 within the weight chamber, thus reducing possible friction contact of the stitching with the material of the sleep mask cover 200 when the weighted mask component 300 is inserted into the internal chamber of the sleep mask cover 200.

In an embodiment, once the weighted mask component 300 is inverted to its proper configuration, the forward panel 302 and the rear panel 304 are further sewn together along the faces of the forward panel 302 and the rear panel 304 to generate a pair of eye panels 308 that may be devoid of any weight material when the weight material is introduced into the weighted mask component 300 through the opening. The eye panels 308 may be located 1.125 inches from an upper edge of the weighted mask component 300. Further, the eye panels 308 may each be sewn approximately two inches from each side of the weighted mask component 300. In an embodiment, the eye panels 308 are each approximately 1.3 inches on each side and are separated by a distance of approximately 1.3 inches. Thus, the innermost side of each eye panel 308 may be located approximate 0.65 inches from the longitudinal center of the weighted mask component 300. It should be noted that while each eye panel 308 is constructed using a square shape, other shapes may be used that may provide optimal comfort to the user of the sleep mask 100 when the weighted mask component 300 is inserted into the sleep mask cover 200 and the sleep mask 100 is worn on the user's head and face.

In an embodiment, the weighted mask component 300 is nine inches in length and 3.5 inches in height from the upper peripheral edge before tapering towards the lower peripheral edge, resulting in a total height of five inches. The bottom edge of the weighted mask component 300 may be similar to the lower peripheral edge of the sleep mask cover 200. For instance, the weighted mask component 300 may be contoured at the lower peripheral edge of the weighted mask component 300 to accommodate the nose bridge of a human user when inserted into the sleep mask cover 200. For example, the distance between the upper peripheral edge and the lower peripheral edge of the weighted mask component 300 may be five inches. Towards the center of the weighted mask component 300, this distance may decrease at a gradual rate to four inches, creating an indentation at the bottom of the weighted mask component 300 at the center that may be used to accommodate the nose bridge of the human user.

Figure 6:
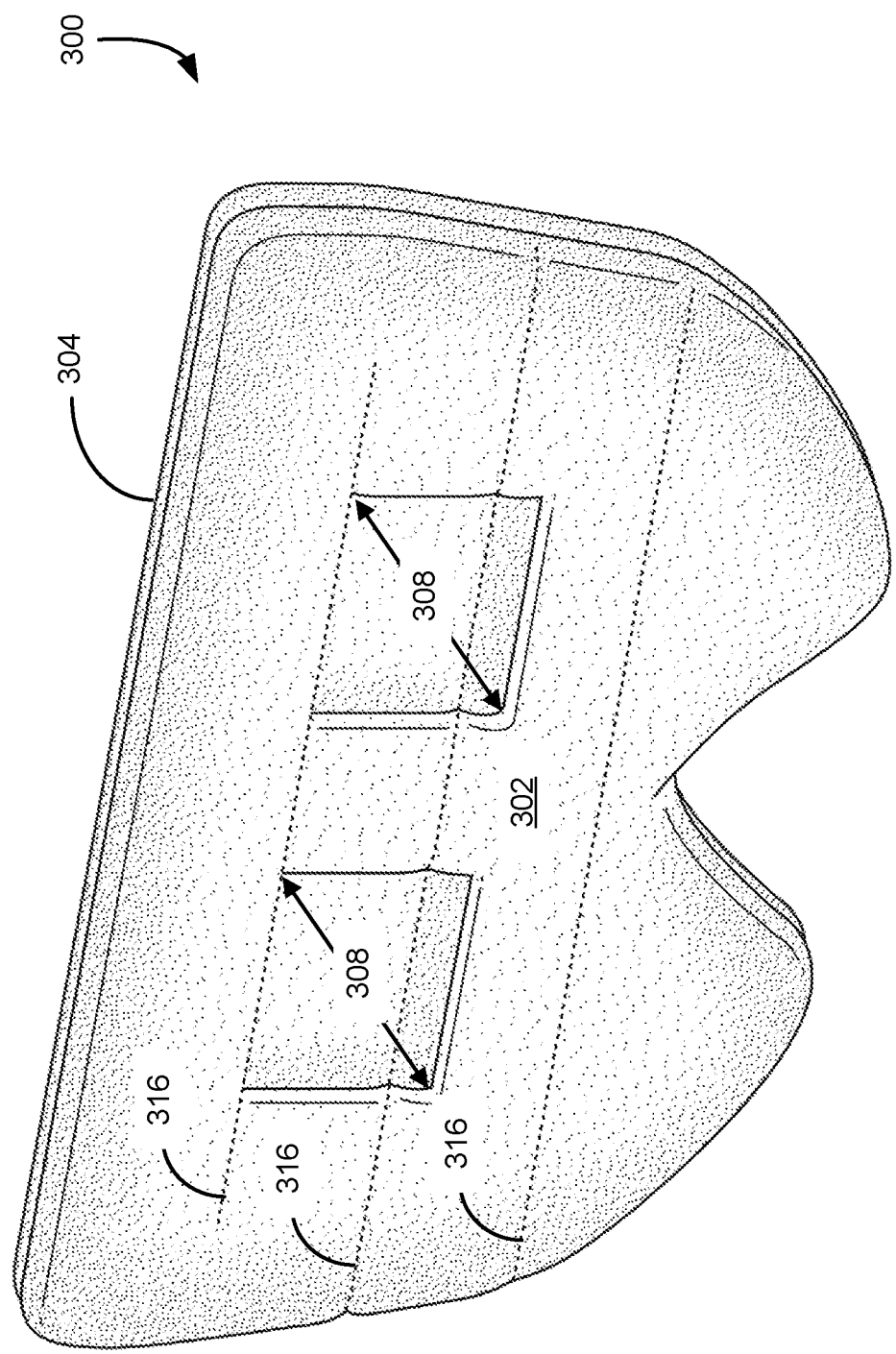
FIG. 6 is a perspective forward view of the weighted mask component of the sleep mask.

In an embodiment, the weighted mask component 300 is further sewn along the length of the forward panel 302 and the rear panel 304 to create banded compartments usable to maintain even distribution of the weight material within the weight chamber. For example, as illustrated in FIG. 6, the weighted mask component 300 may be sewn along the length of forward panel 302 and the rear panel 304 at least in three locations on the weighted mask component 300 to generate at least four banded compartments for the weight material within the weight chamber. As noted above, the eye panels 308 may be sewn into the weighted mask component 300 to prevent any weight material from being present within these eye panels 308. Thus, the distribution of the weight material may be within these banded compartments minus the eye panels 308.

As noted above, the outward facing surfaces of the forward panel 302 and the rear panel 304 may be sewn together along the peripheral edge of each panel 302, 304 while leaving a gap on a side segment of the peripheral edge to create the weighted mask component 300 in an inside-out state with an opening that may be used to invert the weighted mask component 300 into its proper configuration. In an embodiment, once the outward facing surfaces of the forward panel 303 and the rear panel 304 are sewn together along the peripheral edge of each panel 302, 304 with the exception of the opening, the weighted mask component 300 is inverted through the opening, resulting in the weighted mask component 300 being in its proper configuration. Subsequently, the eye panels 308 and the banded compartments may be sewn into the weighted mask compartment 300. As illustrated in the example embodiment of FIG. 3 (and also illustrated in FIG. 6, discussed below), the eye panels 308 are bordered by vertical, non-perimeter lines of stitching that join the forward panel 302 and rear panel 304. The weight material may be introduced into the weight chamber via the opening. The opening may be closed by sewing the forward panel 302 and the rear panel 304 together at the location of the opening. Closure of the opening may prevent the weight material from escaping the weight chamber during use of the sleep mask 100. The weighted mask component 300 may weigh approximately 13 ounces (370 grams) with the weight material present within the weight chamber.

In an embodiment, the weight material comprises a plurality of micro-beads made of glass. The glass composition may comprise, by weight, a mixture of 70 to 75 percent silicon dioxide, 10 to 15 percent sodium oxide, 7 to 9 percent calcium oxide, 2 to 3 percent aluminum oxide, 1 to 1.25 percent magnesium oxide, less than one percent potassium oxide, and less than one percent ferric oxide. It should be noted that while the glass composition described above is used for illustrative purposes, additional and/or alternative materials may be used to generate other glass compositions that may be used to generate the weight material, so long as these other glass compositions enable filling of the weight chamber to achieve the desired weight for the weighted mask component 300 while maintaining even distribution of the weight material within the weight chamber.

In an embodiment, as illustrated in FIG. 7, the weighted mask component 300 further includes a thermal mask component pocket panel that is affixed to the rear panel 304 of the weighted mask component 300 using elastic tape sewn to the sides of the weighted mask component 300 and the bottom seam of the weighted mask component 300. The attachment of the thermal mask component pocket panel to the weighted mask component 300 may result in the creation of a thermal mask component pocket usable to accommodate the thermal mask component 400 of the sleep mask 100. The thermal mask component pocket panel may have a similar shape or profile to that of the weighted mask component 300 in order to prevent any distortion of the shape or profile of the weighted mask component 300 when the thermal mask component 400 is inserted into a thermal mask component pocket created using the thermal mask component pocket panel.

Figure 8:
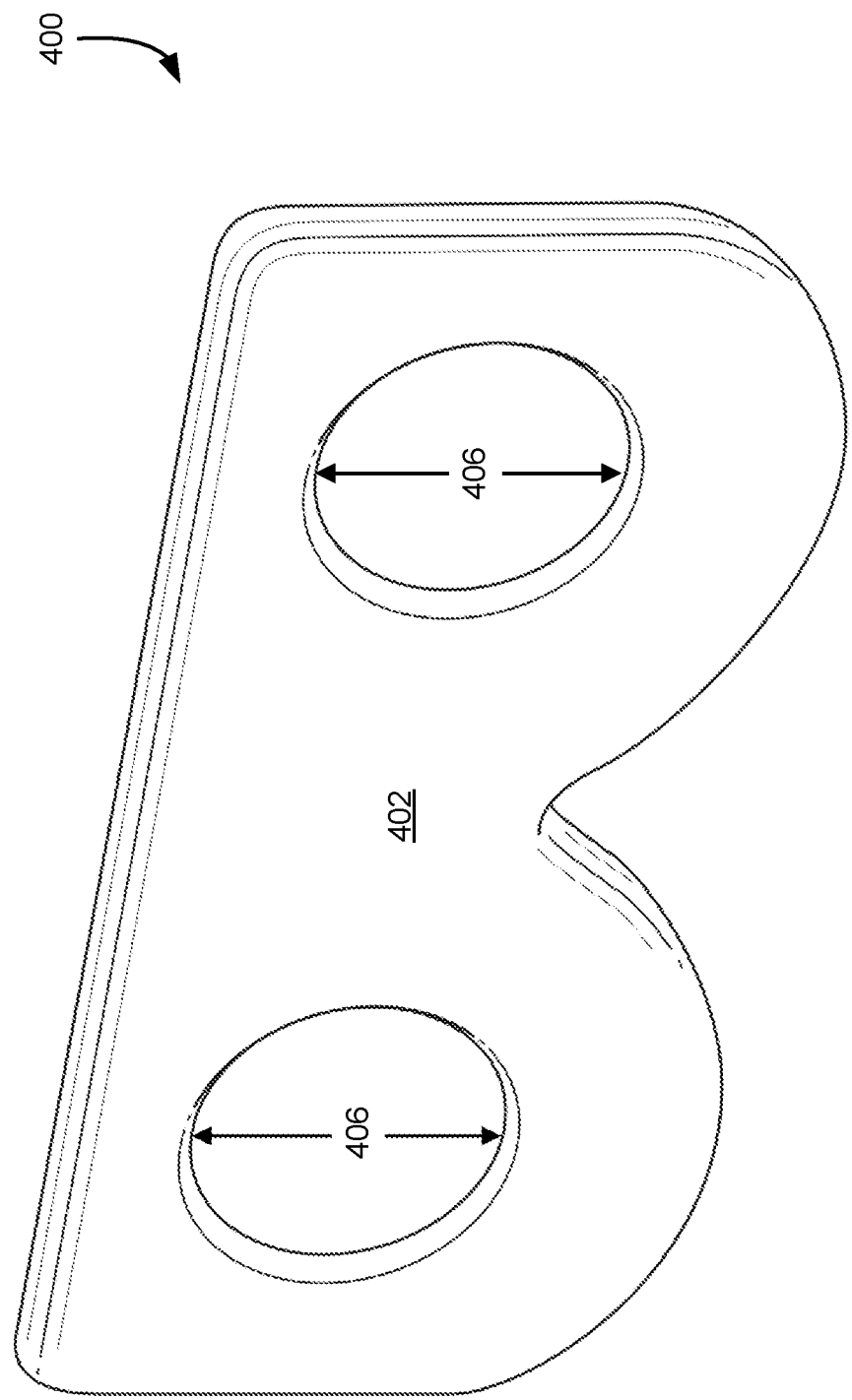
FIG. 8 is a perspective view of the thermal mask component of the sleep mask.

The thermal mask component 400, in an embodiment and as illustrated in FIG. 8, comprises a shell 402 that is used to store a thermal gel usable to heat and/or cool the sleep mask 100 based on a user's preference. For instance, a user of the sleep mask 100 may introduce the thermal mask component 400 to a heating source (e.g., microwave, boiling water, etc.) to cause the thermal mask component 400 to release heat at a gradual rate over time without burning the user of the sleep mask 100. Similarly, the thermal mask component 400 may be introduced to a cooling source (e.g., refrigerator, freezer, etc.) to cause the thermal mask component 400 to provide gradual cooling over time to the user of the sleep mask 100. In an embodiment, the thermal gel is composed, by weight, of 30 to 70 percent water, 0 to 50 percent glycerol, 0.5 to 20 percent sodium polyacrylate, 0 to 10 percent polyethylene glycol (PEG), and 0.01 to 0.5% preservative. It should be noted that while the thermal gel composition described above is used for illustrative purposes, additional and/or alternative materials may be used to generate other thermal gel compositions having a high specific heat capacity. The thermal gel may be injected into the shell 402, whereupon the shell 402 is sealed to prevent expulsion of the thermal gel during use.

In an embodiment, the thermal mask component 400 includes eye cutouts 406 to prevent heating or cooling of a human individual's eyes when the sleep mask 100 is affixed to the human individual's head. The dimensions of the thermal mask component 400 may be selected to match the contours of the weighted mask component 300 when inserted into the thermal mask component pocket through the aforementioned thermal mask component pocket panel of the weighted mask component 300. For instance, the thermal mask component 400 may be designed such that the eye cutouts 406 align with the eye panels 308 of the weighted mask component 300 when inserted into the thermal mask component pocket. As an illustrative example, to ensure that the thermal mask component 400 fits into the thermal mask component pocket of the weighted mask component 300 without distorting the shape and contours of the weighted mask component 300, the thermal mask component 400 may be 8 inches in length and 3 inches in height at either side of the thermal mask component 400. Further, the thermal mask component 400 may have a similar contour to that of the weighted mask component 300 at its bottom edge such that the height of the thermal mask component 400 increases from 3 inches at either side to a maximum height of 3.55 inches at the bottom edge approximately in line with the center of each eye cutout 406. The bottom edge of the thermal mask component 400 may further be contoured at the bottom edge of the thermal mask component 400 to accommodate the nose bridge of a human user. The thermal mask component 400 may weigh approximately 2.5 ounces (70 to 72 grams).

FIG. 2 is a perspective view of the sleep mask cover 200 of the sleep mask 100 with the strap 210 of the sleep mask cover 100 disengaged. As noted above, the sleep mask cover 200 may include a pair of side tabs 208 usable to attach components of a strap 210 that may be used to removably position the sleep mask 100 onto a user's head and face. For instance, the sleep mask cover 200 may include a first strap component 212 that may be sewn into a first side tab of the sleep mask cover 200. This first strap component 212 may include a fastening component that may be removably attached to a second fastening component of the second strap component 214 to engage the fastening mechanism of the strap 210. The second strap component 214 may be sewn into a second side tab of the sleep mask cover 200. This second strap component 214 may include the other fastening component usable to engage the fastening mechanism of the strap 210.

Figure 5:
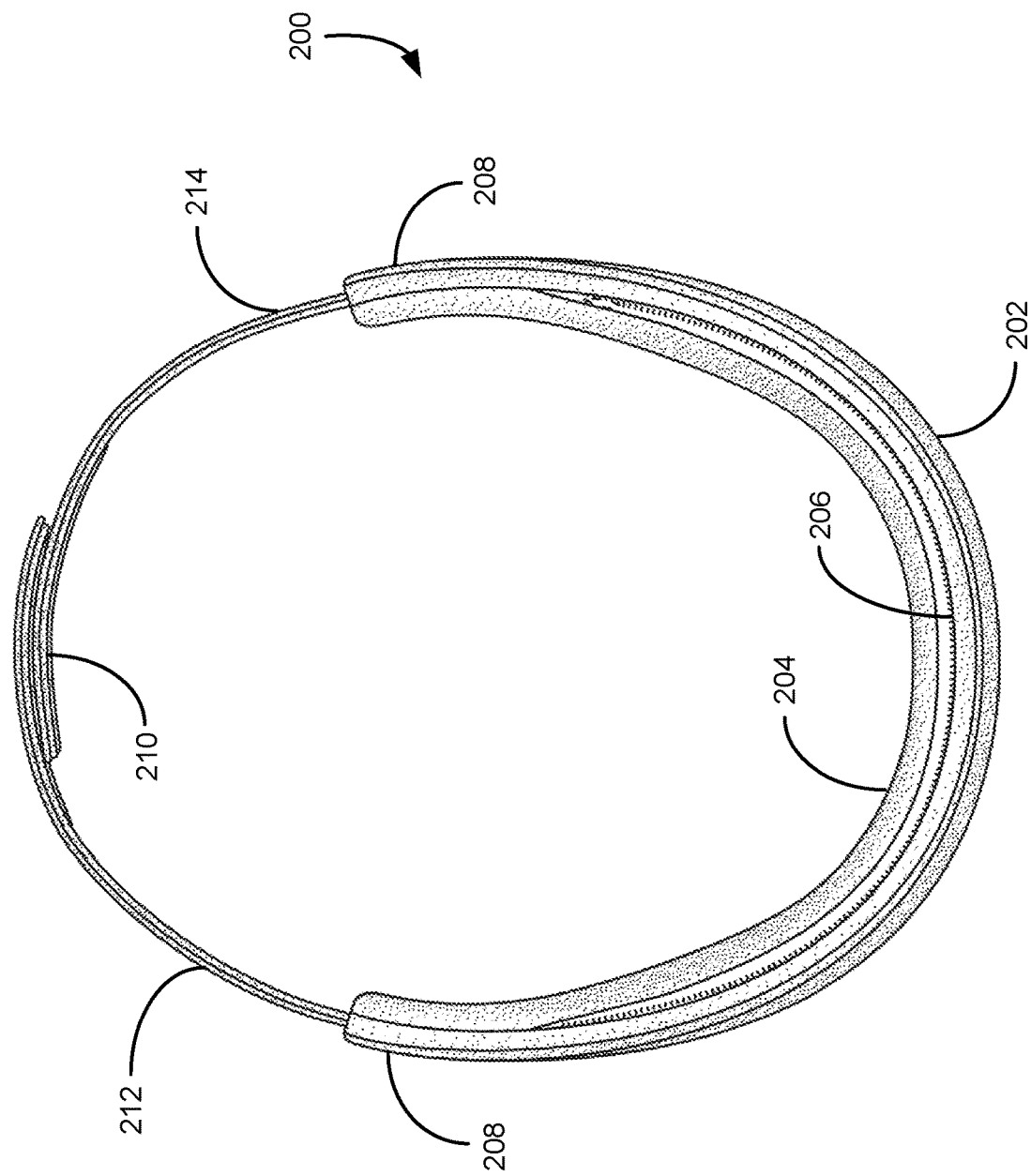
FIG. 5 is a top view of the sleep mask cover of the sleep mask with the strap of the sleep mask cover engaged.

The strap components 212, 214 may be created such that removable attachment of the fastening components of the strap 210 is performed by overlapping a strap component having a fastening component on an outer surface of the strap component with the other strap component having a second fastening component on an inner surface of the other strap component. This may allow a user to adjust the fit of the sleep mask 100 around its head by determining the level of overlap between the strap components 212, 214 for removable attachment of the fastening components. For example, as illustrated in FIG. 5, the first strap component 212, which may have a first fastening component sewn or otherwise adhered to an inner surface of the first strap component 212, may be used to overlap the second strap component 214, which may have a second fastening component sewn or otherwise adhered to an outer surface of the second strap component 214, to removable attach the fastening components and, hence, engage the fastening mechanism of the strap 210.

Figure 3:
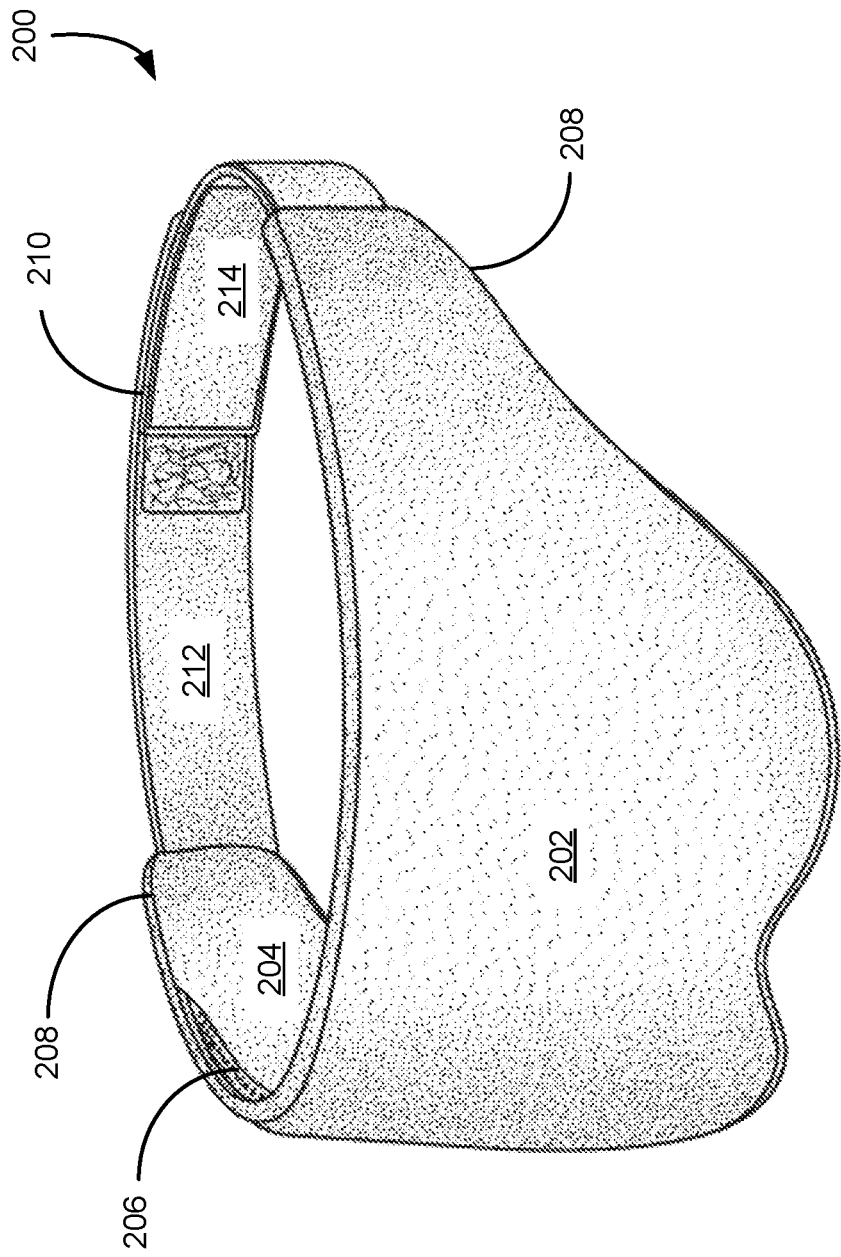
FIG. 3 is a perspective view of the sleep mask cover of the sleep mask with the strap of the sleep mask cover engaged.

FIG. 3 is a perspective view of the sleep mask cover 200 of the sleep mask 100 with the strap components 212, 214 of the strap 210 removably attached to enable positioning of the sleep mask 100 on a human individual's head and face. As illustrated in FIG. 3, the first strap component 212 and the second strap component 214 are removably attached via the fastening mechanism of the strap 210. For instance, the first strap component 212 may comprise, on an interior surface of the first strap component 212, a first fastening component that may be removably attached to a second fastening component of the second strap component 214. This first fastening component includes, in an embodiment, either a fabric strip comprising hooks or a fabric strip comprising loops that may receive the hooks of the other fastening component. This fabric strip may be sewn or otherwise adhered to the interior surface of the first strap component 212. The second strap component 214, in an embodiment, includes, on the outer surface of the second strap component 214, the other fastening component that can be removably attached to the fastening component of the first strap component 212. For example, if the first strap component 212 includes a fabric strip comprising hooks, the fastening component of the second strap component 214 may include a fabric strip, sewn or otherwise adhered to the outer surface of the second strap component 214, comprising a set of loops that may receive the hooks of fabric strip of the first strap component 212.

It should be noted that the configuration of the strap components 212, 214 for removably attaching these strap components 212, 214 presented above is for the purpose of illustration and other configurations may be utilized. For instance, the first strap component 212 may include, on the inner surface of the first strap component 212, a fastening component while the second strap component 214 may include, on the outer surface of the second strap component 214, another fastening component. In another example, the fastening components may be attached to the outermost end of each of the strap components 212, 214 such that the fastening mechanism may be engaged through removable attachment of the fastening components without need to overlap the strap components 212, 214. In another example, the fastening mechanism may be a snapback fastening system whereby either the first strap component 212 or second strap component 214 includes a snap component and the other strap component includes a receiver component that may be removably attached to the snap component to engage the fastening mechanism.

FIG. 4 is a rear view of the sleep mask cover 200 of the sleep mask 100 with the strap components 212, 214 of the strap 210 engaged. As noted above, the front cover component 202 and the rear cover component 204 may be manufactured using pleuche or any other textile materials, such as: cashmere, imitation cashmere, fleece, leather, satin, suede, velvet, fustian, corduroy, flannel, tweed, polyester, micro-fiber, and the like. In an embodiment, the front cover component 202 and the rear cover component 204 can be manufactured using different materials. For example, the front cover component 202 may be manufactured using pleuche while the rear cover component 204 may be manufactured using a material with a smooth surface, such as satin.

In an embodiment, removable engagement of the strap components 212, 214 via the fastening mechanism of the strap 210 causes the side tabs 208 and the cover components 202, 204 to conform to the shape of the object to which the sleep mask 100 is affixed to. For example, when the sleep mask 100 is worn around a human user's head and face, the strap components 212, 214 of the strap 210, the side tabs 208, and the cover components 202, 204 of the sleep mask cover 200 may conform to the contours of the human user's head and face at the various contact points. Thus, the sleep mask 100 may provide a custom circumferential fit around a human user's head and face via adjustment and removable engagement of the strap components 212, 214 via the fastening mechanism of the strap 210.

As illustrated in FIG. 4, the sleep mask cover 200 includes a fastening mechanism 206 that may be used to expose an internal chamber of the sleep mask cover 200 for introduction of the weighted mask component and the thermal mask component. As noted above, the upper peripheral edge of each of the front cover component 202 and the rear cover component 204 may remain unattached to create an opening to the internal chamber of the sleep mask cover 200. The fastening mechanism 206 may be sewn or adhered to the upper peripheral edge of each of the front cover component 202 and the rear cover component 204 along the opening. This fastening mechanism 206 may be used to close the opening, preventing access to the internal chamber of the sleep mask cover 200. Further, if the opening is closed, the fastening mechanism 206 may be disengaged to enable use of the opening to access the internal chamber of the sleep mask cover 200 for insertion or removal of the weighted mask component, the thermal mask component, or any other material.

FIG. 5 is a top view of the sleep mask cover 200 of the sleep mask 100 with the strap 210 of the sleep mask cover 200 engaged. As noted above, the first strap component 212, which may have a first fastening component sewn or otherwise adhered to an inner surface of the first strap component 212, may be used to overlap the second strap component 214, which may have a second fastening component sewn or otherwise adhered to an outer surface of the second strap component 214, to removable attach the fastening components and, hence, engage the fastening mechanism of the strap 210. Each of the first strap component 212 and the second strap component 214 of the strap 210 may be sewn or otherwise adhered to an individual side tab 208 of the sleep mask cover 200. For instance, a first strap component 212 may be sewn into a first side tab of the sleep mask cover 200. The second strap component 214 may be sewn into a second side tab of the sleep mask cover 200.

As noted above, the sleep mask cover 200 may include a fastening mechanism 206 sewn or otherwise adhered to an upper peripheral edge of each of the forward cover component 202 and the rear cover component 204. This fastening mechanism 206 may be used to removably attach the upper peripheral edges of the forward cover component 202 and the rear cover component 204 to close the opening, preventing access to the internal chamber of the sleep mask cover 200. Further, if the opening is closed, the fastening mechanism 206 may be disengaged to allow access to the internal chamber of the sleep mask cover 200 for insertion or removal of the weighted mask component, the thermal mask component, or any other material. As illustrated in FIG. 5, the fastening mechanism 206 may be a zipper, which can be used to removably attach the upper peripheral edges of the front cover component 202 and the rear cover component 204 to close or expose the opening to the internal chamber of the sleep mask cover 200. Other alternatives for the fastening mechanism 206 may be used, such as hook and loop fasteners (e.g., Velcro®, etc.), snap fasteners, buttons, clamps, and the like.

FIG. 6 is a perspective forward view of the weighted mask component 300 of the sleep mask 100. As noted above, the weighted mask component 300 may include a forward panel 302 and a rear panel 304 that may be sewn together along the peripheral edges of each of the forward panel 302 and rear panel 304 to create a weight chamber usable to introduce weight material into the weighted mask component 300. To manufacture the weighted mask component 300, the outward facing surfaces of the forward panel 302 and the rear panel 304 may be sewn together along the peripheral edge of each panel 302, 304 while leaving a gap on a side segment of the peripheral edge. This may result in the creation of the weighted mask component 300 in an inside-out state with an opening that may be used to invert the weighted mask component 300 into its proper configuration and to enable access to the weight chamber.

In an embodiment, once the weighted mask component 300 is inverted to its proper configuration, the forward panel 302 and the rear panel 304 are further sewn together along segments of the faces of the forward panel 302 and the rear panel 304 to generate a pair of eye panels 308 that may be devoid of any weight material when the weight material is introduced into the weighted mask component 300 through the opening. As illustrated in FIG. 6, the eye panels 308 may be structured to have a square or rectangular shape. However, it should be noted that while each eye panel 308, as illustrated in FIG. 6, is constructed using a square shape, other shapes may be used that may provide optimal comfort to the user of the sleep mask 100 when the weighted mask component 300 is inserted into the sleep mask cover 200 and the sleep mask 100 is worn on the user's head and face.

As illustrated in FIG. 6, the bottom edge of the weighted mask component 300 may be similar to the lower peripheral edge of the sleep mask cover 200. For instance, the weighted mask component 300 may be contoured at the lower peripheral edge of the weighted mask component 300 to accommodate the nose bridge of a human user when inserted into the sleep mask cover 200. In an embodiment, the weighted mask component 300 is further sewn along the length of the forward panel 302 and the rear panel 304 to generate dividers 316 within the weighted mask component 300, resulting in banded compartments usable to maintain even distribution of the weight material within the weight chamber. For example, the weighted mask component 300 may be sewn along the length of forward panel 302 and the rear panel 304 at least in three locations on the weighted mask component 300, creating three separate dividers 316. As illustrated in the example embodiment of FIG. 6, a horizontal stitch may serve as a divider 316 for at least three compartments of the weighted mask component. The creation of these dividers 316 may result in the generation of at least four banded compartments for the weight material within the weight chamber. As noted above, the eye panels 308 may be sewn into the weighted mask component 300 to prevent any weight material from being present within these eye panels 308, which is an example of how the stitching that joins the forward panel and rear panel 304 causes a decrease in thickness of the weighted mask component at locations of eyes of a human user thereby causing pressure from the sleep mask on the human user to be greater around the eyes of the human user than directly over the eyes of the human user when the sleep mask is worn by the human user lying down. Thus, the distribution of the weight material may be within these banded compartments minus the eye panels 308.

FIG. 7 is a perspective rear view of the weighted mask component 300 of the sleep mask 100. As noted above, the weighted mask component 300 includes a thermal mask component pocket panel 310 that is attached to the rear panel 304 of the weighted mask component 300 using elastic tape 314 sewn or otherwise adhered to the sides of the weighted mask component 300. The attachment of the thermal mask component pocket panel 310 to the weighted mask component 300 may result in the creation of a thermal mask component pocket usable to accommodate the thermal mask component of the sleep mask 100. The thermal mask component pocket panel may have a similar shape or profile to that of the weighted mask component 300 in order to prevent any distortion of the shape or profile of the weighted mask component 300 when the thermal mask component is inserted into a thermal mask component pocket created using the thermal mask component pocket panel 310.

The thermal mask component pocket panel 310 may be manufactured using non-toxic materials that may be resistant to thermal changes caused by the heating or cooling of the thermal mask component. Thus, in an embodiment, the thermal mask component pocket panel 310 is created using the same material utilized to create the forward panel 302 and rear panel 304 of the weighted mask component 300. The length and elasticity of the elastic tape 314 may be selected such that insertion of the thermal mask component into the thermal mask component pocket is possible while maintaining the position of the thermal mask component within the pocket while the sleep mask is in use. The positioning of the pocket may allow for alignment of the eye cutouts of the thermal mask component with the eye panels of the weighted mask component 300 when the thermal mask component is present in the pocket.

FIG. 8 is a perspective view of the thermal mask component 400 of the sleep mask 100. The thermal mask component 400, in an embodiment, comprises a shell 402 that is used to store a thermal gel usable to heat and/or cool the sleep mask 100 based on a user's preference. For instance, a user of the sleep mask 100 may introduce the thermal mask component 400 to a heating source (e.g., microwave, boiling water, etc.) to cause the thermal mask component 400 to release heat at a gradual rate over time without burning the user of the sleep mask 100. Similarly, the thermal mask component 400 may be introduced to a cooling source (e.g., refrigerator, freezer, etc.) to cause the thermal mask component 400 to provide gradual cooling over time to the user of the sleep mask 100. The thermal gel may be injected into the shell 402, whereupon the shell 402 is sealed to prevent expulsion of the thermal gel during use.

In an embodiment, the thermal mask component 400 includes eye cutouts 406 to prevent heating or cooling of a human individual's eyes when the sleep mask 100 is affixed to the human individual's head. The dimensions of the thermal mask component 400 may be selected to match the contours of the weighted mask component when inserted into the thermal mask component pocket through the aforementioned thermal mask component pocket panel of the weighted mask component. For instance, the thermal mask component 400 may be designed such that the eye cutouts 406 align with the eye panels of the weighted mask component when inserted into the thermal mask component pocket. Further, the thermal mask component 400 may have a similar contour to that of the weighted mask component at its bottom edge. The bottom edge of the thermal mask component 400 may further be contoured at the bottom edge of the thermal mask component 400 to accommodate the nose bridge of a human user.

FIG. 9 is a perspective of the sleep mask 100 as worn on the head 500 of a human individual. An individual may insert the weighted mask component and/or the thermal mask component into the sleep mask cover via an opening exposed via disengagement of the fastening mechanism 206 of the sleep mask cover. To affix the sleep mask 100 on the head 500 of a human individual, the human individual may removably attach the strap components of the strap 210 around its head 500 to provide a circumferential fit over the eyes over the nose bridge of the human individual.

The specification and drawings are to be regarded in an illustrative rather than a restrictive sense. However, it will be evident that various modifications and changes may be made thereunto without departing from the broader spirit and scope of the invention as set forth in the claims. Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a," "an," "the," and similar referents in the context of describing the disclosed embodiments (especially in the context of the following claims) are to be construed to cover both the singular and the plural, unless otherwise indicated or clearly contradicted by context. The terms "comprising," "having," "including," and "containing" are to be construed as open-ended terms (i.e., meaning "including, but not limited to,") unless otherwise noted. The term "connected," where unmodified and referring to physical connections, is to be construed as partly or wholly contained within, attached to, or joined together, even if there is something intervening. Recitation of ranges of values are merely intended to serve as a shorthand method of referring individually to each separate value falling within the range, unless otherwise indicated and each separate value is incorporated into the specification as if it were individually recited. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Conjunctive language, such as phrases of the form "at least one of A, B, and C," or "at least one of A, B and C," is understood with the context as used in general to present that an item, term, etc., may be either A or B or C, or any nonempty subset of the set of A and B and C, unless specifically stated otherwise or otherwise clearly contradicted by context. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present. In addition, unless otherwise noted or contradicted by context, the term "plurality" indicates a state of being plural (e.g., "a plurality of items" indicates multiple items). The number of items in a plurality is at least two, but can be more when so indicated either explicitly or by context.

The use of any examples, or exemplary language (e.g., "such as") provided, is intended merely to better illuminate embodiments of the invention and does not pose a limitation on the scope of the invention unless otherwise claimed. No language in the specification should be construed as indicating any non-claimed element as essential to the practice of the invention.

Embodiments of this disclosure are described, including the best mode known to the inventors for carrying out the invention. Variations of those embodiments may become apparent to those of ordinary skill in the art upon reading the foregoing description. The inventors expect skilled artisans to employ such variations as appropriate and the inventors intend for embodiments of the present disclosure to be practiced otherwise than as specifically described. Accordingly, the scope of the present disclosure includes all modifications and equivalents of the subject matter recited in the claims appended hereto as permitted by applicable law. Moreover, although above-described elements may be described in the context of certain embodiments of the specification, unless stated otherwise or otherwise clear from context, these elements are not mutually exclusive to only those embodiments in which they are described; any combination of the above-described elements in all possible variations thereof is encompassed by the scope of the present disclosure unless otherwise indicated or otherwise clearly contradicted by context.

All references, including publications, patent applications, and patents, cited are hereby incorporated by reference to the same extent as if each reference were individually and specifically indicated to be incorporated by reference and were set forth in its entirety.

What is claimed is:

1. A sleep mask, comprising:
    a sleep mask cover comprising:
        a front cover component;
        a rear cover component; and
        an opening; and
    a weighted component that is removably inserted into the opening of the sleep mask cover, composed of a thermally resistant material, and configured to be placed between the front cover component and the rear cover component, the weighted component comprising:
        a forward panel;
        a rear panel;
        a plurality of separate banded compartments each having a weighted material placed within the banded compartments, each of the plurality of banded compartments being separated internally of the weighted component, each of the plurality of separate banded compartments disposed between the forward panel and rear panel;
        a plurality of dividers to separate each of the plurality of separate banded compartments so that the weighted material is distributed within each of the banded compartments,
            wherein the plurality of dividers comprise stitches provided between the forward panel and rear panel of the weighted component,
            wherein the banded compartments each extend along a length of the weighted component, and
            wherein each of the banded compartments are disposed in parallel; and
        a thermal mask component pocket panel affixed to the rear panel of the weighted mask component configured to accommodate a thermal mask component,
            wherein the thermal mask component is configured to retain heat when the thermal mask component is introduced to a heating source, and
            wherein the thermal mask component pocket panel is affixed to the rear panel via elastic tape adhered to two sides of the weighted mask component.

2. The sleep mask of claim 1, wherein the weighted material further comprises a plurality of micro-beads made of a glass composition, the glass composition comprising, by weight, a mixture of 70 to 75 percent silicon dioxide, 10 to 15 percent sodium oxide, 7 to 9 percent calcium oxide, 2 to 3 percent aluminum oxide, 1 to 1.25 percent magnesium oxide, less than one percent potassium oxide, and less than one percent ferric oxide.

3. The sleep mask of claim 1, wherein the front cover component is composed of a first material and the rear cover component is composed of a second material, and wherein the first material and the second material are different materials.

4. The sleep mask of claim 1, further comprising:
    a panel provided at an eye portion of the weighted component distinct from the plurality of separate banded compartments, wherein the panel contains no weighted material provided within the panel.

5. The sleep mask of claim 4, wherein the panel comprises two panels and the plurality of separate banded compartments containing the weighted material surround the two panels.

6. The sleep mask of claim 1, further comprising:
    a first strap component attached to the sleep mask cover at a first side of the sleep mask cover; and a second strap component attached to the sleep mask cover at a second side of the sleep mask cover opposite the first side.

7. The sleep mask of claim 1, further comprising:
a closing mechanism configured to open and close the opening, wherein the opening is provided at a top portion of the sleep mask cover between the front cover component and the rear cover component.

8. The sleep mask of claim 1, wherein the weighted component has a substantially similar size and shape as the sleep mask cover.

9. The sleep mask of claim 1, wherein the weighted material comprises beads made of glass.

10. A sleep mask, comprising:
a sleep mask cover comprising:
a front cover component; and
a rear cover component; and
a weighted component, composed of a thermally resistant material, provided between the front cover component and the rear cover component, the weighted component comprising:
a top portion having a weighted material configured to be placed above a user's eyes;
a bottom portion having the weighted material configured to be placed below a user's eye, wherein the weighted material in the bottom portion is within a separate divided compartment from the weighted material in the top portion, and wherein the weighted material comprises a plurality of beads;
a middle portion between the top portion and bottom portion, the middle portion configured to be placed on a user's eyes, wherein a first section of the middle portion does not contain any weighted material;
a plurality of dividers that separate the top portion, middle portion and bottom portion such that the weighted material is distributed within the top portion, the bottom portion and a second section of the middle portion,
wherein the plurality of dividers extend along a length of the weighted component,
wherein the plurality of dividers are parallel, and
wherein the top portion, the first section of the middle portion, the second section of the middle portion, and the bottom portion are banded;
a thermal mask component pocket panel affixed to the rear panel of the weighted mask component configured to accommodate a thermal mask component,
wherein the thermal mask component is configured to retain heat when the thermal mask component is introduced to a heating source, and
wherein the thermal mask component pocket panel is affixed to the rear panel via elastic tape adhered to at least two sides of the weighted mask component.

11. The sleep mask of claim 10, further comprising:
two panel areas in the first section of the middle portion configured to be placed on a user's eyes, wherein the two panel areas do not contain the weighted material and the second section of the middle portion comprises the weighted material.

12. The sleep mask of claim 11, wherein the first section of the middle portion is disposed between the top portion and the second section of the middle portion, and the second section of the middle portion is disposed between the first section of the middle portion and the bottom portion.

13. The sleep mask of claim 10, further comprising:
an opening provided between the front cover component and the rear cover component, wherein the weighted component is configured to be removably inserted within the opening.

14. The sleep mask of claim 13, further comprising:
a closing mechanism configured to open and close the opening, wherein the opening is provided at a top portion of the sleep mask cover between the front cover component and the rear cover component.

15. The sleep mask of claim 10, wherein the plurality of beads are a plurality of micro-beads made of a glass composition, the glass composition comprising, by weight, a mixture of 70 to 75 percent silicon dioxide, 10 to 15 percent sodium oxide, 7 to 9 percent calcium oxide, 2 to 3 percent aluminum oxide, 1 to 1.25 percent magnesium oxide, less than one percent potassium oxide, and less than one percent ferric oxide.

16. A sleep mask, comprising:
a sleep mask cover comprising:
a front cover component; and
a rear cover component,
wherein the front cover component is composed of a first material and the rear cover component is composed of a second material, and
wherein the first material and the second material are different materials; and
a weighted component provided between the front cover component and the rear cover component, the weighted component comprising:
a first portion having a weighted material,
wherein the weighted material comprises a plurality of beads; and
a second portion configured to be placed on a user's eyes, the second portion not containing the weighted material;
wherein the first portion comprises at least a first chamber and a second chamber separated internally in the weighted component;
a forward panel;
a rear panel;
a plurality of dividers provided between the forward panel and the rear panel and the plurality of dividers configured to prevent the weighted material in the first portion from entering the second portion,
wherein the plurality of dividers are disposed parallel along a length of the weighted component, such that at least the first portion and the second portion are banded; and
a thermal mask component pocket panel affixed to the rear panel of the weighted mask component configured to accommodate a thermal mask component,
wherein the thermal mask component is configured to retain heat when the thermal mask component is introduced to a heating source, and
wherein the thermal mask component pocket panel is affixed to the rear panel via elastic tape adhered to at least two sides of the weighted mask component.

17. The sleep mask of claim 16, wherein the second portion comprises:
at least two panel areas not containing any weighted material.

18. The sleep mask of claim 17, wherein the plurality of beads are a plurality of micro-beads made of a glass composition, the glass composition comprising, by weight, a mixture of 70 to 75 percent silicon dioxide, 10 to 15 percent sodium oxide, 7 to 9 percent calcium oxide, 2 to 3 percent aluminum oxide, 1 to 1.25 percent magnesium oxide, less than one percent potassium oxide, and less than one percent ferric oxide.

19. The sleep mask of claim 1, wherein the plurality of dividers comprises three dividers and the plurality of separate banded compartments comprises four separate banded compartments.

20. The sleep mask of claim 1, wherein a shape of the thermal mask component pocket panel is similar to a shape of the weighted mask component.

\* \* \* \* \*